United States Patent [19]

Alexander et al.

[11] Patent Number: 5,423,781
[45] Date of Patent: Jun. 13, 1995

[54] METHOD AND APPARATUS FOR MEASURING THE VOLUME OF A FLUID

[75] Inventors: David A. Alexander, Alabaster; Martin J. McCutcheon, Vestavia Hills, both of Ala.

[73] Assignee: The UAB Research Foundation, Birmingham, Ala.

[21] Appl. No.: 881,151

[22] Filed: May 11, 1992

[51] Int. Cl.⁶ .............................................. A61M 5/00
[52] U.S. Cl. ..................... 604/318; 604/319; 604/322; 128/771; 177/DIG. 5; 248/309.4; 206/818
[58] Field of Search ................. 604/65, 317, 318, 319, 604/322, 326, 403, 404, 407; 128/771; 177/DIG. 5; 403/DIG. 1; 248/206.5, 309.4; 206/818; 220/236

[56] References Cited

U.S. PATENT DOCUMENTS

| | | | |
|---|---|---|---|
| 2,957,596 | 10/1960 | Rehborg | 248/206.5 |
| 3,610,459 | 10/1971 | Hanson | 206/818 |
| 3,642,122 | 2/1972 | Von Ende | 206/818 |
| 3,982,716 | 9/1976 | Trees | 248/309.4 |
| 4,402,373 | 9/1983 | Comeau | 128/771 |
| 4,523,083 | 6/1985 | Hamilton | 206/818 |
| 4,650,464 | 3/1987 | Ruiz et al. | 604/49 |
| 4,654,029 | 3/1987 | D'Antonio | 128/771 |
| 4,772,256 | 9/1988 | Lane et al. | 604/4 |
| 4,775,360 | 10/1988 | Lane et al. | 604/4 |
| 4,781,707 | 11/1988 | Boenringer et al. | 604/317 |
| 4,798,578 | 1/1989 | Ranford | 604/4 |
| 4,922,922 | 5/1990 | Pollack et al. | 128/771 |
| 5,054,726 | 10/1991 | Mattox | 248/206.5 |
| 5,078,683 | 1/1992 | Sancoff | 604/67 |
| 5,116,312 | 5/1992 | Blankenship | 604/66 |

OTHER PUBLICATIONS

Blankenship et al. "Clinical Application of Closed-Loop Postoperative Autotransfusion", *Medical Progress through Technology* First Prog 142:1–5, 1989.

Cosgrove et al. "An Improved Technique for Autotransfusion of Shed Mediastinal Blood", *Ann. Thorac. Surg.* 440:519, 1985.

Johnson et al. "The Efficacy of Postoperative Autotransfusion in Patients Undergoing Cardiac Operations" *Ann. Thorac. Surg.* 36:178, 1983.

Sheppard et al. "Cardiac Surgical Intensive Care Computer System", *Federation Proceedings* 33:2326–2318, 1974.

Sheppard et al. "Automated Treatment of Critically Ill Patients Following Operation", *Annals of Surgery* 168:596–604, 1968.

*Primary Examiner*—Ralph A. Lewis
*Attorney, Agent, or Firm*—Needle & Rosenberg

[57] ABSTRACT

A method and apparatus for measuring the volume of a fluid using a load cell transducer in which the container holding the fluid, such as a cardiotomy reservoir, is firmly but detachably engaged to an adapter for a load cell transducer. Further, this invention relates to a method and apparatus for detecting the presence and alignment of the container on a load cell so as to allow accurate measurement of the volume of a fluid contained within the container. The apparatus generally includes a magnetic ring on a bottom-facing surface of the container, a metallic ring on an upward-facing surface of the mounting adapter for the load cell and a sensor capable of detecting a magnetic field.

13 Claims, 3 Drawing Sheets

METHOD AND APPARATUS FOR MEASURING THE VOLUME OF A FLUID

BACKGROUND OF THE INVENTION

The present invention relates to a method and apparatus for measuring the volume or weight of a fluid, such as measuring the volume of blood or urine in a transfusion or autotransfusion system employed in a cardiac intensive care unit (CICU). More particularly, the invention relates to the measurement of the volume of a fluid in a container, such as a cardiotomy or urine resvoir, employing a load cell transducer.

During the immediate recovery of post-operative cardiovascular surgery patients, CICU nurses are responsible for carrying out several tasks. These include the management of the patient's heart rate and rhythm, ventilation, blood pressure, renal function, temperature, and monitoring of chest tube and urine drainage. In the case of serious post operative bleeding, close monitoring of chest tube drainage is critical and replacement of lost blood volume is required. Autotransfusion involves the reinfusion of a patient's own blood as opposed to the transfusion of bank blood. Although intraoperative and postoperative blood conservation techniques have decreased the use of bank blood for cardiac surgical patients, the increasing number of surgical procedures has placed a strain on the bank blood supply. One procedure to reduce this strain is postoperative autotransfusion, the return of blood shed from the mediastinum or thoracic cavity following surgery. The efficacy and safety of postoperative autotransfusion has been documented (Johnson et al., Ann. Thorac. Surg. 1983; 36:178). Furthermore, autotransfusion is the safest form of transfusion therapy because there is no risk of alloimmunization, hepatitis, acquired immunodeficiency syndrome (AIDS), or other complications possible with bank blood. The operation and efficacy of an autotransfusion system is described in U.S. patent application Ser. No. 07/431,296, which is hereby incorporated by reference in its entirety in order to more fully describe the state of the art to which this invention pertains.

Existing autotransfusion systems usually include a cardiotomy reservoir for the collection of blood shed from the patient. The reservoir, which may collect body fluids other than blood, is associated with a lead cell transducer which measures the volume of fluid in the reservoir. A disadvantage of current systems is that the connection between the body fluid container and the lead cell transducer is passive and is susceptible to being bumped or pulled out of alignment. A further disadvantage of existing systems is that there is no automated means for detecting the presence of the reservoir on the lead cell mounting adapter or the proper alignment of the reservoir on the mounting adapter.

A still further disadvantage of existing systems is that there is no automated means for protecting the lead cell transducer from damage resulting from overweighing due to bumping or excess force during the seating of the container on the mounting adapter for the lead cell transducer.

Therefore, there exists a need for a fluid collection system in which the container and lead cell adapter are firmly attached during operation. Further, there exists a need for means, particularly automated means, for detecting the placement and alignment of a container capable of holding a fluid on a lead cell transducer. There also exists a need for protecting the lead cell transducer from damage due to improper movement or positioning of the fluid container.

Throughout this application, various publications are referenced. The disclosures of these publications in their entireties are hereby incorporated by reference into this application in order to more fully describe the state of the art to which this invention pertains.

SUMMARY OF THE INVENTION

The present invention relates to a method and apparatus for firmly but detachably engaging a container, such as a cardiotomy reservoir, to an adapter for a load cell transducer. Further, this invention relates to a method and apparatus for detecting the presence and alignment of a container on a load cell so as to allow accurate measurement of the volume of a fluid contained within the container. The apparatus generally includes a magnetic ring on a bottom-facing surface of the container, a metallic ring on an upward-facing surface of the mounting adapter for the load cell and a sensor capable of detecting a magnetic field.

In particular, the present invention provides a method and apparatus for measuring the volume or weight of a fluid using a load cell transducer having a mounting adapter positioned on top of the transducer, and a container capable of receiving a fluid, the container being detachably engageable with the mounting adapter. The apparatus further includes a first magnetic means attached to the container and a second magnetic means attached to the mounting adapter such that the first magnetic means engages the second magnetic means when the container is properly seated on the mounting adapter on the transducer. The magnetic engagement of the container and the mounting adapter provides positive engagement and properly balanced seating of the container on the transducer. The container of the present invention is properly seated on the mounting adapter of the load cell transducer when the first magnetic means on the container is magnetically engaged with the second magnetic means on the mounting adapter so that the container is positioned so as to allow accurate measurement of the container and its fluid contents by the load cell transducer.

In the preferred embodiment of this apparatus, the first magnetic means is a magnet located on a downward-facing surface of the container and the second magnetic means is a metallic element located on an upward-facing surface of the mounting adapter on the transducer such that the magnet can magnetically engage the metallic element. An alternative embodiment involves positioning the magnet on the upward-facing surface of the mounting adapter and the metallic element on a downward-facing surface of the container.

The apparatus of this invention can also include a means for sensing whether the container is engaged with the mounting adapter so as to determine whether the container is properly seated on the transducer. The sensing means can be Hall effect sensors or other means that sense the presence of a magnetic field. The sensors will preferably also be capable of detecting the orientation of the magnetic field.

DETAILED DESCRIPTION OF THE INVENTION

The preferred embodiments of the present invention are now described with reference to the drawings, wherein like parts are designated with like numerals throughout.

The measuring apparatus of the present invention can be used to measure the volume or weight of any fluid. However, measurement of fluid in a medical context, such as shed blood or urine, is especially contemplated. For instance, an automated autotransfusion system can include the apparatus of the present invention. Shed fluid drains from the patient through drainage tubes into a container, which is preferably a cardiotomy reservoir converted for use as a container for postoperative mediasfinal drainage (Cosgrove et al., Ann. Thorac. Surg. 1985, 40:519).

Figure 1:
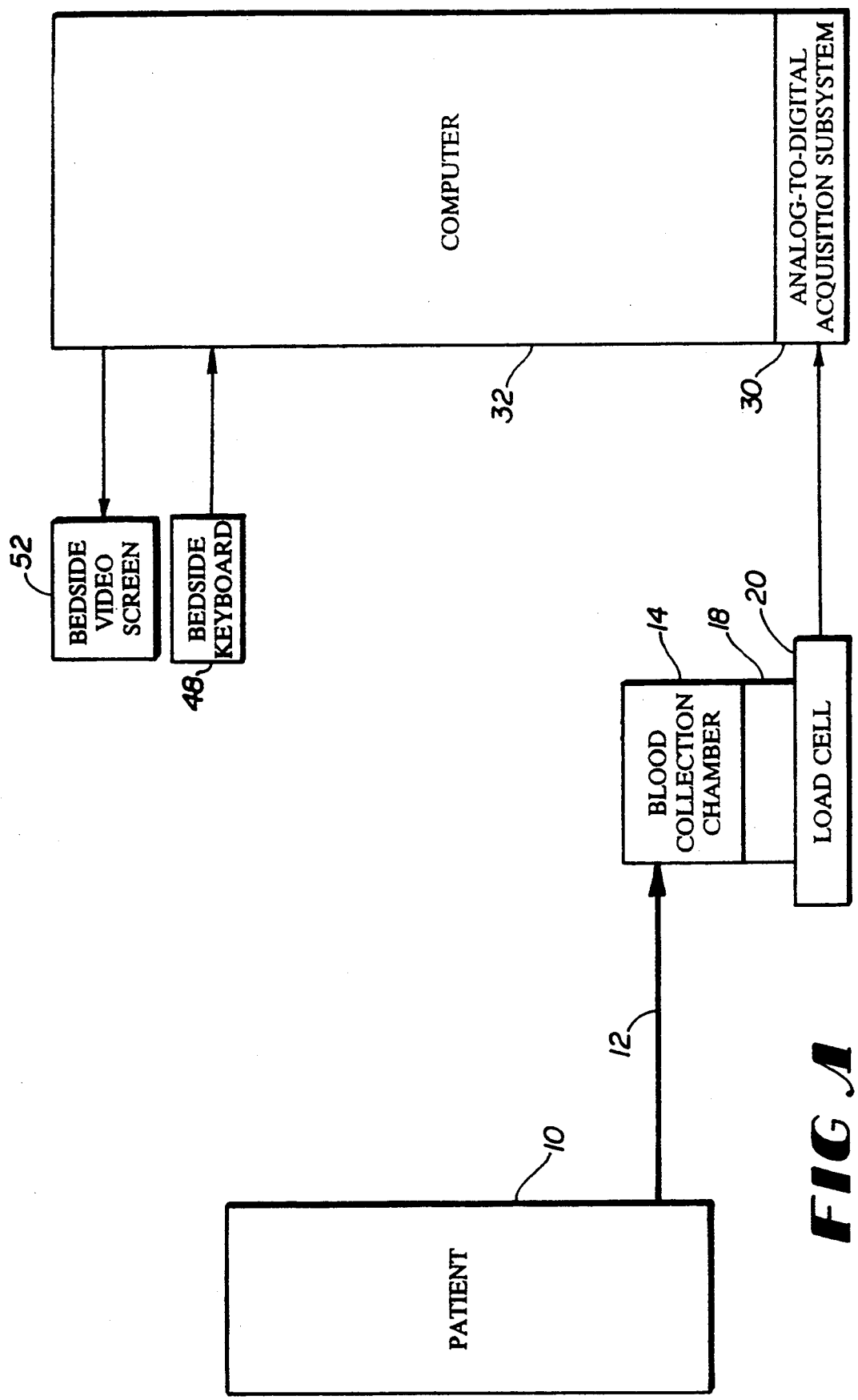
FIG. 1 shows a block diagram of an embodiment according to the present invention.

Referring to FIG. 1, the container 14 can be transported with the patient from the operating room to the intensive care unit following surgery and placed on an adapter 18 for a load cell transducer 20, which holds container 14 in place so that load cell transducer 20 can measure the force exerted by the container 14 and its fluid. The fluid from a fluid source 10, such as patient undergoing autotransfusion, flows via conduit 12 into the container 14. The weight of the container 14 is measured and converted to a voltage proportional to the weight of container 14 by load cell 20, preferably a Gould Slatham UTC3 load cell with mechanical attenuator or AL Design Inc. ALD-DLC-51b load cell. Load cell transducer 20 generates an analog signal corresponding to weight of the container 14. This signal is transmitted, via intervening circuitry, to the analog-to-digital acquisition subsystem 30 of computer 32. Bedside video screen 52, which is connected to computer 32 via intervening circuitry, allows for the visual display of parameters associated with the measurement of the volume or weight of the fluid in the container, including whether the container is placed properly on the adapter and in correct alignment. A bedside keyboard 48 is electronically connected to computer 32 to allow bedside control of computer 32.

Figure 2:
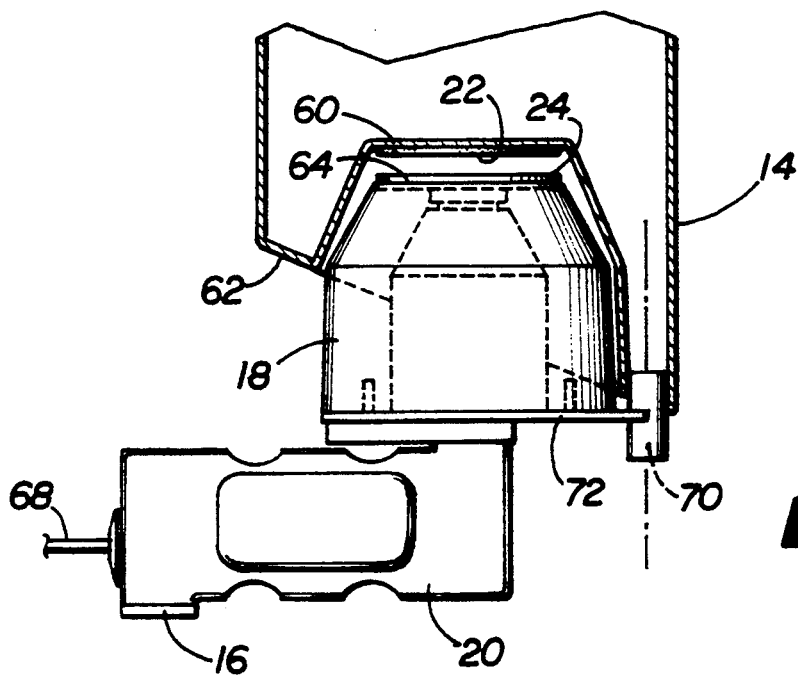
FIG. 2 shows a partially cut-away side elevational view of one embodiment of the fluid measuring apparatus according to the present invention.

As shown in FIG. 2, fluid in container 14, such as a cardiotomy reservoir, exerts a vertical force on the load cell transducer 20, located on a container mounting adapter 18 for the load cell transducer 20 on the measurement stand 16. Other forces (which are non-fluid) include the weight of the container or reservoir and stress forces in the lines that supply or remove fluid from the container. The total vertical force (fluid component + non-fluid component) is converted from the mechanical force into an electrical signal by the load cell transducer. The electrical signals (digitized) are then processed by signal conditioning circuits preferably located in the measuring stand 16 or attached to the second magnetic means. The fluid component will vary as fluid is added and/or removed from the container while the non-fluid component will remain constant. During the calibration procedure, the actual fluid level is determined so that the constant non-fluid component can be subtracted out, allowing the true fluid level to be determined.

Figure 3:
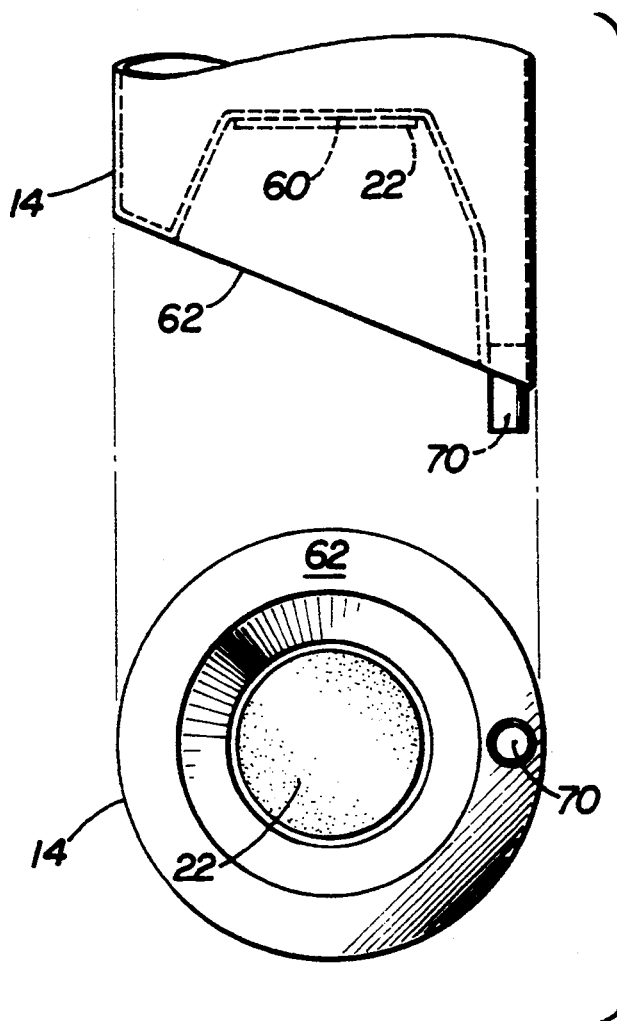
FIG. 3 shows side elevational and bottom plan views of one embodiment of the downward-facing surface of a container having a first magnetic means according to the present invention.

The container used in the present invention can be a cardiotomy container, a urine container or other container that can be adapted to engage a mounting adapter for a load cell transducer. The container has a downward-facing surface on its bottom, such as downward-facing surface 60 as depicted in FIG. 3. The bottom of container 14 is, for the most part, typical of known cardiotomy and urine reservoirs for the collection of postoperative shed blood or urine. The containers of the present invention depart from the typical containers in that they include a first magnetic means 22, preferably a magnet, positioned so as to be engageable with a second magnetic means 24, preferably a metallic element, located on the mounting adapter 18 for the load cell transducer 20. The first magnetic means may be of any shape, but is preferably a magnet in the shape of a ring positioned as shown in FIGS. 2 and 3. The first magnetic means of the present apparatus can alternatively be placed on other downward-facing surfaces of the container, for example, the underside of shelf 62 extending from the side of the container. In such alternative embodiments, the mounting adapter with the second magnetic means thereon will be shaped and positioned to allow at least partial engagement of the second magnetic means with the first magnetic means.

The downward-facing surface on the container can be the lowest exterior surface of the container as in a flat-bottomed container. Preferably, the downward-facing surface will be the recessed bottom of the container, such as is shown in FIGS. 2 and 3. This recessed bottom configuration enhances the stability of the container when seated on the mounting adapter. The downward-facing surface can, alternatively, be located elsewhere on the exterior of the container.

In an alternative embodiment the first magnetic means is a metallic element located on a downward-facing surface of the container and the second magnetic means is a magnet located on an upward-facing surface of the mounting adapter. In this alternative embodiment, if Hall effect sensors are included, they may be located on the metallic element on the container, and the Hall effect sensing circuit may also be on the container.

The magnet of the present invention is, preferably, a ceramic magnet because ceramic magnets are generally stronger, and thus provides a better contact and a stronger engagement with the metallic element. Preferably, a ceramic magnet, such as part number 63B2312276X2 (Magnetic Sales, Inc., CA) can be used. Magnets of other types, including flexible rubber magnets and stiff magnets that are capable of generating a magnetic field of about 50 to 400 gauss, preferably about 100–250 gauss, most preferably about 200 gauss at a distance of up to about ⅛ inch from the surface of the magnet can be used. The upper limit is determined by the mechanics of the system. That is, the magnet must disengage from the metallic element before the force on the load cell exceeds the maximum rated capacity of the load cell. The magnet may be placed on downward-facing surface 60 of the container when the bottom of the container will be in contact with the mounting adapter, as shown in FIG. 2. Alternatively, the magnet may be placed on the downward-facing surface of a shelf extending from the side of the container when the shelf will be in contact with the adapter for the load cell transducer. The magnet is, preferably, hot melted onto the container, though other methods of attachment can be used, as is appreciated by those skilled in the art.

Figure 4A:
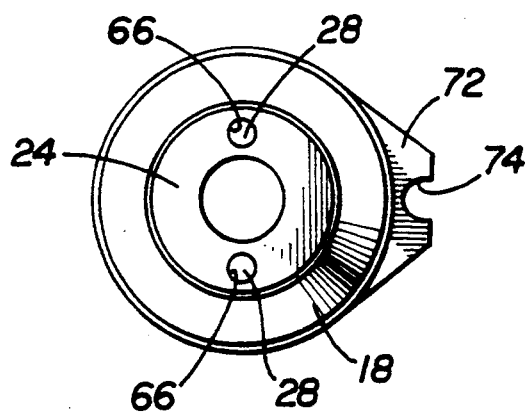
FIG. 4a shows a top plan view of one embodiment of the upward-facing surface of a mounting adapter having a second magnetic means according to the present invention.
Figure 4B:
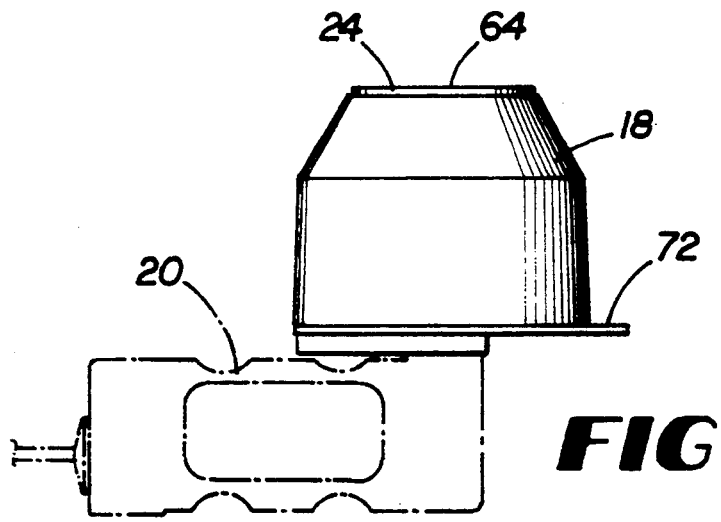
FIG. 4b shows a side elevational view of one embodiment of the mounting adapter and load cell transducer according to the present invention.

As shown in FIGS. 2, 4a and 4b, the mounting adapter 18 of the instant invention is shaped to mechanically engage container 14 so that an upward-facing surface 64 of the mounting adapter is in registry with the downward-facing surface of container 14 to which the first magnetic means is attached. The second magnetic means 24 is attached on top of surface 64 so as to allow engagement of first and second magnetic means 22 and 24, respectively, when container 14 is positioned on adapter 18. The mounting adapter is of a shape and construction sufficient to support a fluid container 14 of the present invention. Generally, the shape and construction of the mounting adapter of this invention will be typical of mounting adapters for cardiotomy vessels and the like, which are currently known and used. However, as described above, the mounting adapter of the present invention departs from what is typical in that it includes a second magnetic means 24, preferably a metallic element, capable of contacting the first magnetic means 22, preferably a magnet, on a downward-facing surface of the container 14. The second magnetic means 24 attached to the mounting adapter 18 should, preferably, be of a shape complimentary to the shape of the first magnetic means 22 on a downward-facing side of container 14, and must at least, be in partial registry with the first magnetic means 22 so as to be capable of detachably engaging the first magnetic means. The second magnetic means 24 can be attached to the adapter upward-facing surface 64 by hot melting or by any other suitable means of attachment.

As shown in FIGS. 2, 4a and 4b, mounting adapter 18 of the present invention can also include a stabilizer bar 72 to guide the container onto adapter 18 and having a notch 74 therein to hold outlet port 70 on the container 14 for more stable seating.

The metallic element of this invention can also include a sensor 28 capable of sensing the presence of a magnetic field. Such sensors 28, preferably can be Hall effect sensors, but can be other known sensors that sense the presence, intensity and/or orientation of a magnetic field. Preferably, at least two Hall effect sensors are used, such as those capable of detecting a magnetic field of about 50 to 250 gauss, preferably about 80 to 150 gauss, most preferably about 100 gauss for example, such as part number UGN31404 (Sprague Semiconductors, Worcester, Mass.), at up to about $\frac{1}{8}$ inch from the source of the field. If Hall effect sensors are sensitive enough and/or the magnetic field is strong enough to energize the sensors at $\frac{1}{2}$ inches or greater from source of the magnetic field, the Hall effect sensing circuit may not be able to detect proper sealing. Thus, although the magnetic strength might be appropriate to provide proper seating, misalignment could not be detected. The sensors 28 can be placed variously on the metallic element of mounting adapter 18, but the preferred placement, as shown in FIG. 4, is to orient two sensors approximately 180° apart from each other on the metallic element. In this manner, misalignment of the container 14, such as by tipping, can be sensed.

The metallic element can by any metallic structure capable of engaging the magnet of the instant invention in a detachable manner. That is, the interaction between the magnet and the metallic element must be strong enough to hold the container 14 firmly on the adapter 18 so that the container remains firmly engaged to the adapter when subjected to disturbing forces, such as the bumping of a cardiotomy reservoir typically found in a hospital setting. When the second magnetic means 24 is a metallic element, the metallic element is preferably a stainless steel plate, such as a 0.125 inch stainless steel plate, which optionally has notches 66 thereon to accommodate at least two Hall effect sensors 28. The notches 66 in the metallic element should be positioned such that the Hall effect sensors 28 in the notches are in registry with the magnet on the container. These notches should be sufficiently spaced apart from each other on the metallic element so that the Hall effect sensors therein can detect the proper seating of the container 14 on the mounting adapter 18.

In the preferred embodiment, the notches 66 containing the Hall effect sensors 28 are 180° apart from each other as depicted in FIG. 4a. However, any arrangement will accomplish the purposes of this invention in which the sensors are sufficiently far apart so that, when the container 14 is misaligned on the mounting adapter 18, at least one sensor is not energized by the magnetic field even though other sensors may be. Thus, the Hall effect sensors signal the proper seating of the container on the mounting adapter when both sensors become energized by the presence of a magnetic field of sufficient strength. If the container is tilted to an unacceptable degree, such as to raise one side of the first magnetic means more than about $\frac{1}{8}$ of an inch from the proper resting position on the second magnetic means, only one of the Hall effect sensors will be energized, thus signaling the improper seating condition of the container. If there is no container seated on the mounting adapter neither sensor will be energized.

Figure 5:
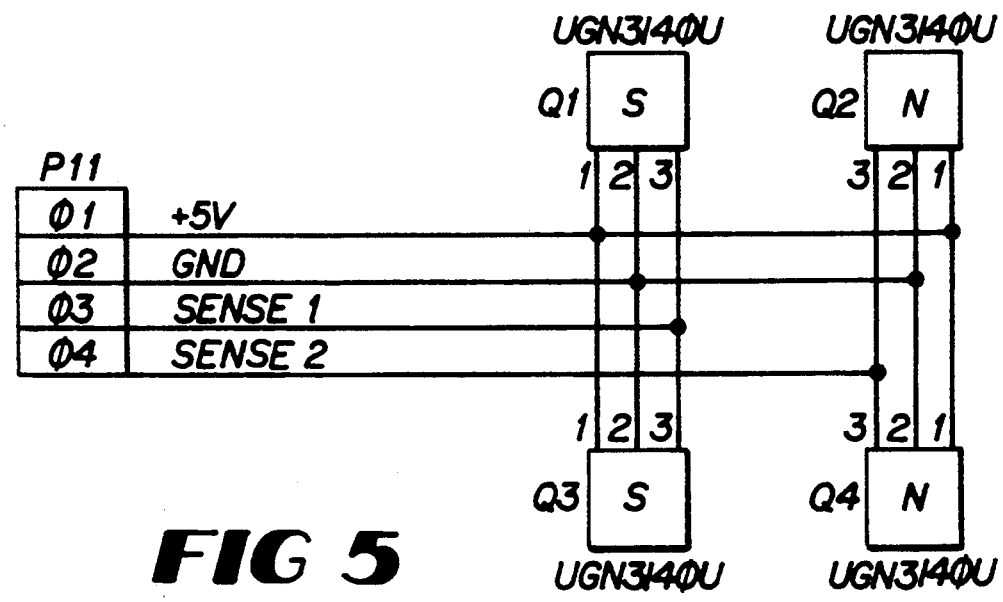
FIG. 5 shows one embodiment of the Hall effect sensing circuit according to the present invention.

In the preferred embodiment, the metallic element will also include a Hall effect sensing circuit, as exemplified in FIG. 5, which preferably is mounted on a PC board within the adapter. In the preferred embodiment, the Hall effect sensing circuit detects whether one or more Hall effect sensors are energized. Thus, this sensing circuit allows the determination of whether the container is properly mounted on the adapter.

Further, the Hall effect sensing circuit acts as a switch to activate the load cell transducer when the appropriate Hall effect sensors are energized. Alternatively, input from this circuit to the computer in the computer monitoring control system will determine whether or not to activate the load cell transducer. Because the transducer is a sensitive instrument, it can be easily damaged by excess force exerted on the transducer during seating and removal of the container from the mounting adapter. In the present invention, this is less of a problem because the transducer will not be activated unless the appropriate sensors, such as both sensors, are energized. Thus, the transducer will not be switched on unless the container is properly seated on the mounting adapter for the load cell transducer. Additionally, if the container is bumped or pulled out of proper alignment with the mounting adapter during subsequent operation, the above described switch is able to de-activate the load cell transducer to prevent damage to it.

The sensors of the present invention may also detect the orientation of a magnetic field. Particularly, if the sensor is oriented with north facing up, it will be energized by a magnet oriented with its south pole facing down, and vice versa, but a north up sensor orientation will not be energized by a north pole down oriented magnet.

The apparatus of this invention allows for an improved method, particularly an improved automatic method, of measuring the volume of a fluid using a load cell transducer. Using the fluid volume measuring apparatus described above, secure attachment of the container to the load cell transducer can be accomplished prior to determination of the volume so as to provide for a more accurate volume determination. Further, the presence of the container and the correct seating or orientation of the container on the adapter can be verified prior to calculation of the fluid volume.

Thus, this invention provides an improved method for automatically measuring the volume of a fluid in a container in which digitally-coded signals are transmitted from a load cell transducer to a computer having output means. In particular, the method of the present invention includes a) providing a first magnetic means attached to the container; b) providing a load cell transducer mounting adapter positioned on top of the transducer, wherein a second magnetic means is attached to the mounting adapter such that the first magnetic means engages the second magnetic means when the container is properly seated on the mounting adapter; c) placing the fluid container on the mounting adapter so as to seat the container; and d) automatically calculating the fluid volume in the container, such as by the method disclosed in U.S. Ser. No. 07/431,296.

Additionally, prior to the automatically calculating the fluid volume in the container, in order to detect the presence of the container on the adapter and to determine whether the container is aligned correctly so that the container is properly seated, the method of the present invention further provides the steps of e) providing at least two Hall effect sensors located within the second magnetic means; f) providing a Hall effect sensing circuit for sensing whether the container is engaged with the mounting adapter and whether the container is properly seated thereon; g) automatically sensing whether the at least two Hall effect sensors are energized; h) if all of the at least two Hall effect sensors are energized, proceeding with the automatic calculation of the fluid volume; and i) if at least one of the at least two Hall effect sensors is not energized, replacing the container on the mounting adapter so as to seat the container and repeating the automatically sensing step until the container is seated properly.

Further, the method can include the steps of j) following step c), automatically ascertaining the weight corresponding to the voltage output of the load cell transducer; k) comparing the weight ascertained in step j) to the weight of the container to verify the presence of the container on the load cell adapter. That is, the automatic measuring system can verify that a container with a first magnetic means is correctly placed on the adapter as opposed to the presence of just a first magnetic means without the container being seated on the adapter.

Although the present method and apparatus have been described with reference to specific details of certain embodiments thereof, it is not intended that such details should be regarded as limitations upon the scope of the invention except as and to the extent that they are included in the accompanying claims.

What we claim is:

1. An apparatus for measuring the volume of a fluid using a load cell transducer, comprising:
   a) a mounting adapter to be positioned on top of the transducer;
   b) a container capable of receiving a fluid, wherein the container is detachably engageable with the mounting adapter;
   c) a first magnetic means attached to the container;
   d) a second magnetic means attached to the mounting adapter such that the first magnetic means enrages the second magnetic means when the container is properly seated on the mounting adapter on the transducer; and
   e) means for sensing whether the container is engaged with the mounting adapter so as to determine whether the container is properly seated thereon, wherein the means for sensing whether the container is engaged with the mounting adapter senses the presence of a magnetic field.

2. The apparatus of claim 2, wherein the first magnetic means is a magnet located on a downward-facing surface of the container and the second magnetic means is a metallic element located on an upward-facing surface of the mounting adapter on the transducer, such that the magnet can magnetically engage the metallic element.

3. The apparatus of claim 2, wherein the magnet is a ceramic magnet.

4. The apparatus of claim 2, wherein the magnet is a flexible rubber type magnet.

5. The apparatus of claim 2, wherein the magnet generates a field strength of about 200 gauss at a distance of up to about $\frac{1}{8}$ inch from the surface of the magnet.

6. The apparatus of claim 2, wherein the metallic element is a stainless steel plate shaped so as to be capable of detachably engaging the magnet.

7. The apparatus of claim 1, wherein the first magnetic means is a metallic element located on a downward-facing surface of the container and the second magnetic means is a magnet located on an upward-facing surface of the mounting adapter.

8. An apparatus for measuring the volume of a fluid using a load cell transducer, comprising:
   a) a mounting adapter to be positioned on top of the transducer;
   b) a container capable of receiving a fluid., wherein the container is detachably engageable with the mounting adapter;
   c) a first magnetic means attached to the container;
   d) a second magnetic means attached to the mounting adapter such that the first magnetic means engages the second magnetic means when the container is properly seated on the mounting adapter on the transducer; and
   e) means for sensing whether the container is engaged with the mounting adapter so as to determine whether the container is properly seated thereon, wherein the sensing means comprise a Hall effect sensor on the second magnetic means.

9. The apparatus of claim 7, wherein the Hall effect sensor is in a notch on the second magnetic means.

10. An apparatus for measuring the volume of a fluid using a load cell transducer, comprising:
   a) a mounting adapter to be positioned on top of the transducer;
   b) a container capable of receiving a fluid, wherein the container is detachably engageable with the mounting adapter;
   c) a first magnetic means attached to the container;
   d) a second magnetic means attached to the mounting adapter such that the first magnetic means engages the second magnetic means when the container is properly seated on the mounting adapter on the transducer; and
   e) means for sensing whether the container is engaged with the mounting adapter so as to determine whether the container is properly seated thereon, wherein the sensing means comprise at least two Hall effect sensors spaced apart on the second magnetic means.

11. An apparatus for measuring the volume of a fluid using a load cell transducer, comprising:
   a) a mounting adapter to be positioned on top of the transducer;
   b) a container capable of receiving a fluid, wherein the container is detachably engageable with the mounting adapter;
   c) a first magnetic means attached to the container;
   d) a second magnetic means attached to the mounting adapter such that the first magnetic means engages the second magnetic means when the container is properly seated on the mounting adapter on the transducer; and
   e) means for sensing whether the container is engaged with the mounting adapter so as to determine whether the container is properly seated thereon, wherein the sensing means comprise two Hall effect sensors placed 180 degrees apart on the second magnetic means on the mounting adapter.

12. In a method for automatically measuring the volume of a fluid in a container employing the step of transmitting digitally-coded signals from a load cell transducer to a computer having output means, the improvement comprising the steps of:
   a) providing a first magnetic means attached to the container;
   b) providing a load cell transducer mounting adapter positioned on top of the transducer, wherein a second magnetic means is attached to the mounting adapter such that the first magnetic means engages the second magnetic means when the container is properly seated on the mounting adapter;
   c) placing the fluid container on the mounting adapter so as to seat the container;
   d) providing at least two Hall effect sensors located within the second magnetic means;
   e) providing a Hall effect sensing circuit for sensing whether the container is engaged with the mounting adapter and whether the container is properly seated thereon;
   f) automatically sensing whether the at least two Hall effect sensors are energized;
   g) if all of the at least two Hall effect sensors are energized, automatically calculating the fluid volume in the container; and
   h) if at least one of the at least two Hall effect sensors is not energized, replacing the container on the mounting adapter so as to seat the container and repeating the automatically sensing step until the container is seated properly.

13. The method of claim 12, further comprising the steps of:
   i) following step c), automatically ascertaining the weight corresponding to the voltage output of the load cell transducer;
   j) comparing the weight ascertained in step j) to the weight of the container to verify the presence of the container on the load cell adapter.

* * * * *